US010349985B1

(12) United States Patent
Kriete et al.

(10) Patent No.: US 10,349,985 B1
(45) Date of Patent: Jul. 16, 2019

(54) UNIVERSAL PEDICLE SCREW REMOVAL DEVICE AND RELATED METHODS

(71) Applicant: DEANNALYN, INC., Clermont, FL (US)

(72) Inventors: Deanna Kriete, Clermont, FL (US); John Kriete, Leesburg, FL (US)

(73) Assignee: DEANNALYN, INC., Clermont, FL (US)

( * ) Notice: Subject to any disclaimer, the term of this patent is extended or adjusted under 35 U.S.C. 154(b) by 153 days.

(21) Appl. No.: 15/011,756

(22) Filed: Feb. 1, 2016

Related U.S. Application Data

(60) Provisional application No. 62/110,027, filed on Jan. 30, 2015.

(51) Int. Cl.
  *A61B 17/70* (2006.01)
  *A61B 17/88* (2006.01)
(52) U.S. Cl.
  CPC ...... *A61B 17/7082* (2013.01); *A61B 17/8872* (2013.01)

(58) Field of Classification Search
  CPC .................................................. A61B 17/7082
  See application file for complete search history.

(56) References Cited

U.S. PATENT DOCUMENTS

| 2008/0221583 A1* | 9/2008 | Sharifi-Mehr | A61B 17/7032 |
| | | | 606/104 |
| 2012/0253355 A1* | 10/2012 | Murray | A61B 17/8888 |
| | | | 606/104 |

* cited by examiner

*Primary Examiner* — Olivia C Chang
(74) *Attorney, Agent, or Firm* — Allen Dyer Doppelt & Gilchrist PA

(57) ABSTRACT

A pedicle screw removal device comprises a rod having a first end and a second end opposite the first. A clamping member is located at the first end of the rod, and a handle is located at the second end. The clamping member is configured to remove a pedicle screw via clamping to a pedicle screw socket. To remove a pedicle screw, the rod is inserted into a pedicle screw socket until a screw engagement surface on the first end portion of the rod is met by a head of the pedicle screw. The clamping member is lowered to a desired position and clamped to the pedicle screw socket. Rotating the handle unscrews the pedicle screw while the screw engagement surface is pressing on the screw head.

13 Claims, 12 Drawing Sheets

US 10,349,985 B1

UNIVERSAL PEDICLE SCREW REMOVAL DEVICE AND RELATED METHODS

CROSS-REFERENCE TO RELATED APPLICATION

The present application claims the benefit of U.S. Provisional Patent Application Ser. No. 62/110,027, filed on Jan. 30, 2015, the contents of which are herein incorporated by reference in their entirety.

FIELD OF THE INVENTION

The present invention relates to orthopedic devices, more particularly to pedicle screws, and more particularly to pedicle screw removal devices.

BACKGROUND OF THE INVENTION

Spinal pain can result from the wearing of vertebral joints over time. Surgery performed to reduce this spinal pain often involves a combination of polyaxial pedicle screws and rods to create a spinal fixation system. Often, a surgeon will use a certain tool to remove a certain type of pedicle screw. This increases the complexity and reduces the efficiency of a surgery. Various tools have been developed for pedicle screw removal, but their deficiencies suggest that further improvements can be realized.

SUMMARY OF THE INVENTION

In view of the foregoing, it is an object of the present invention to provide an improved pedicle screw removal device and related methods. According to one embodiment of the invention, the pedicle screw removal device includes a rod having a first end and a second end opposite the first. A clamping member is located at the first end and a handle at the second end. The clamping member is configured to remove a pedicle screw by clamping to a pedicle screw socket.

According to another embodiment of the invention, a method of removing a pedicle screw using the pedicle screw removal device includes inserting the rod into a pedicle screw socket until a screw engagement surface on the first end of the rod is met by the head of the pedicle screw. The clamping member is lowered to a desired position and clamped to the pedicle screw socket. The handle is rotated to remove the pedicle screw while the screw engagement surface presses on the screw head.

These and other objects, aspects and advantages of the present invention will be better appreciated in view of the drawings and following detailed description of preferred embodiments.

DETAILED DESCRIPTION OF A PREFERRED EMBODIMENT

Figure 1:
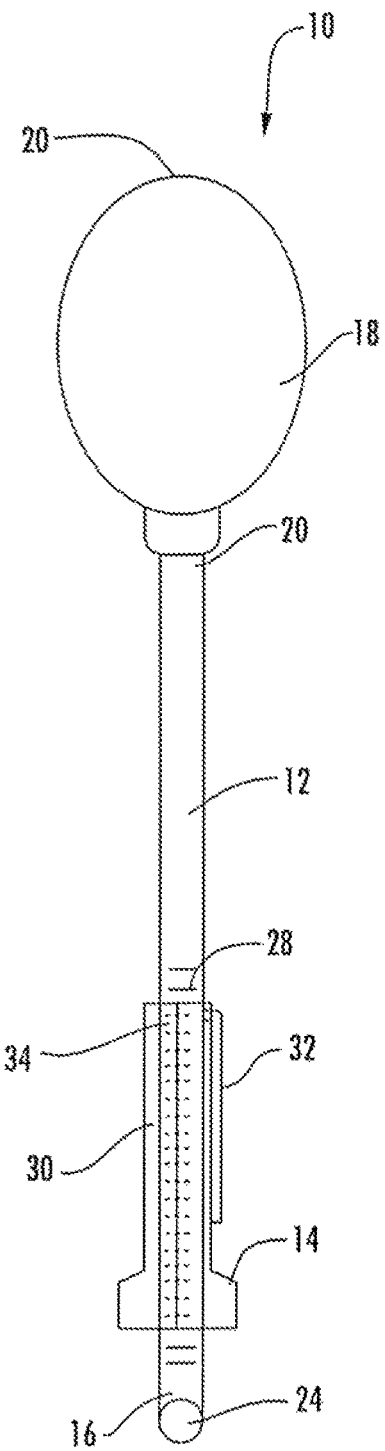
FIG. 1 is a perspective view of a pedicle screw removal device, according to an embodiment of the present invention.
Figure 2:
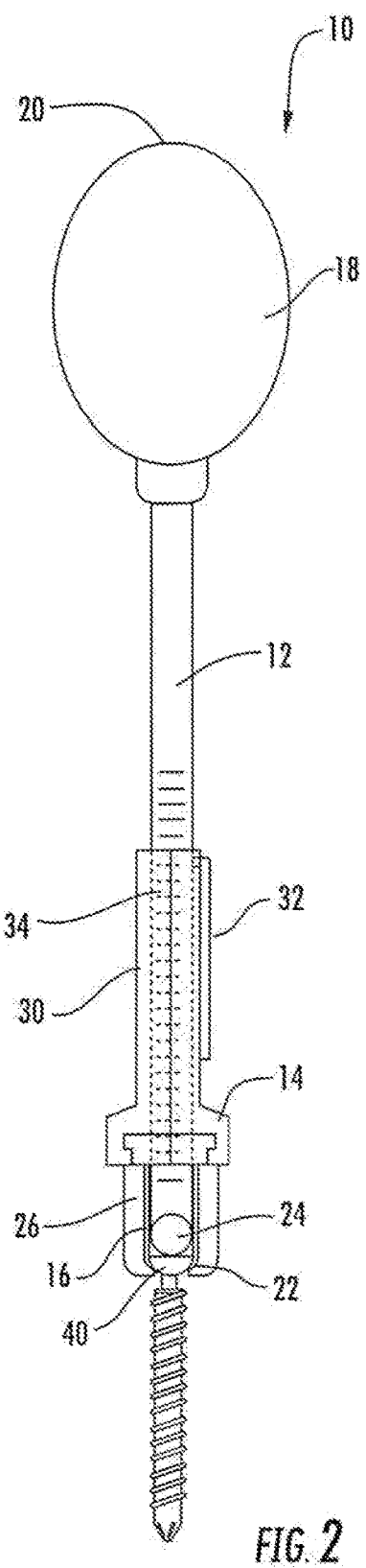
FIG. 2 is a sectional view of the pedicle screw removal device of FIG. 1.
Figure 3:
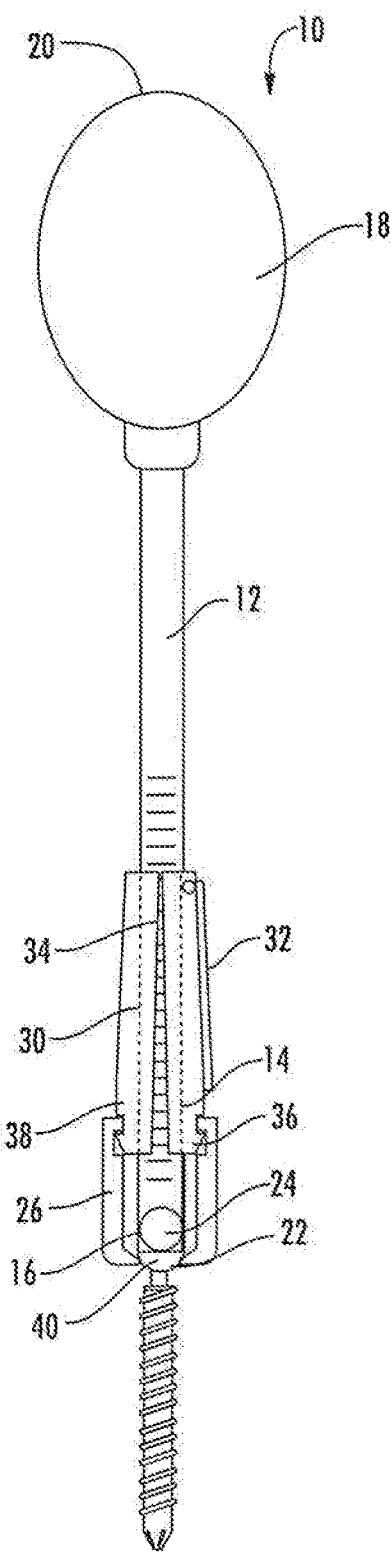
FIG. 3 is another sectional view of the pedicle screw removal device of FIG. 1.
Figure 4:
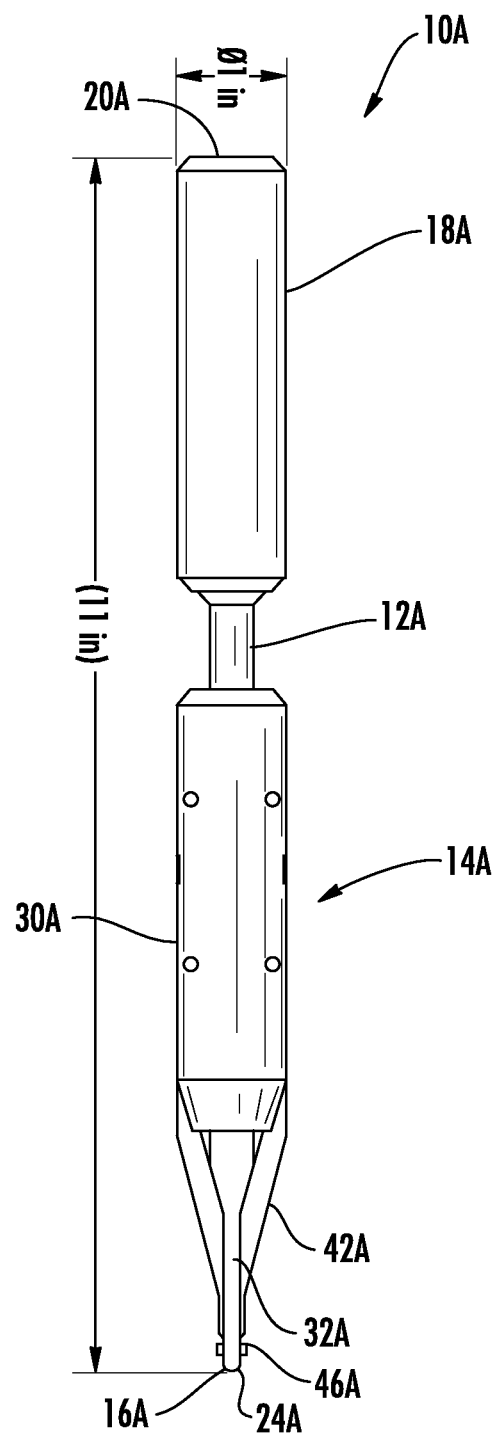
FIG. 4 is a side view of a pedicle screw removal device, according to another embodiment of the present invention.
Figure 5:
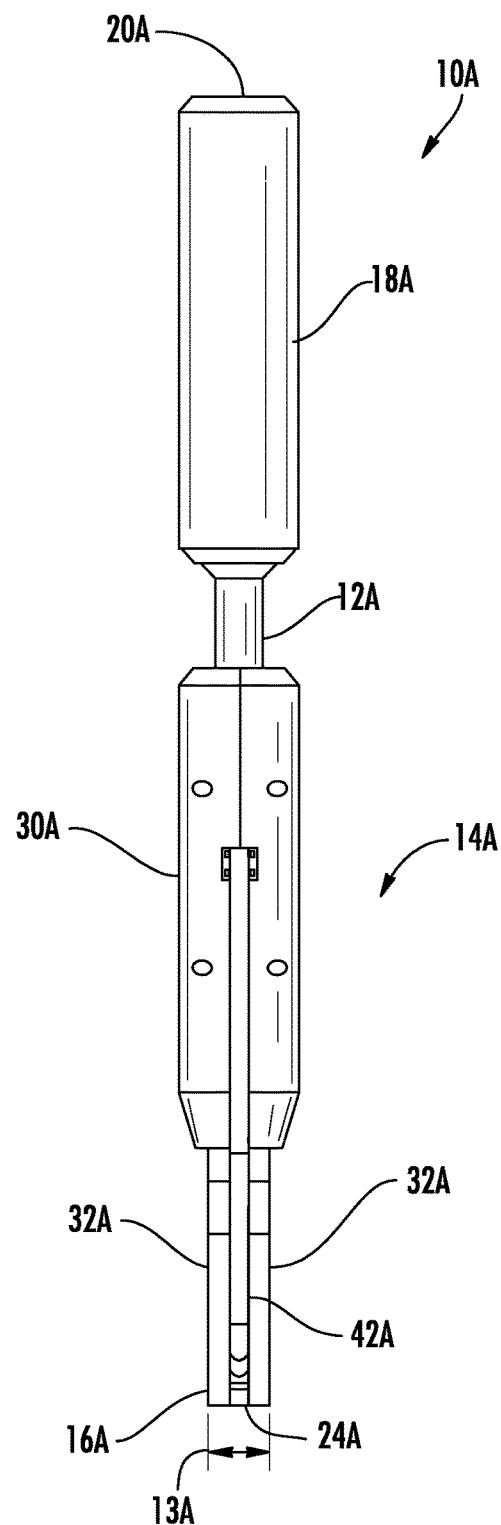
FIG. 5 is another side view of the pedicle screw removal device of FIG. 4.
Figure 6:
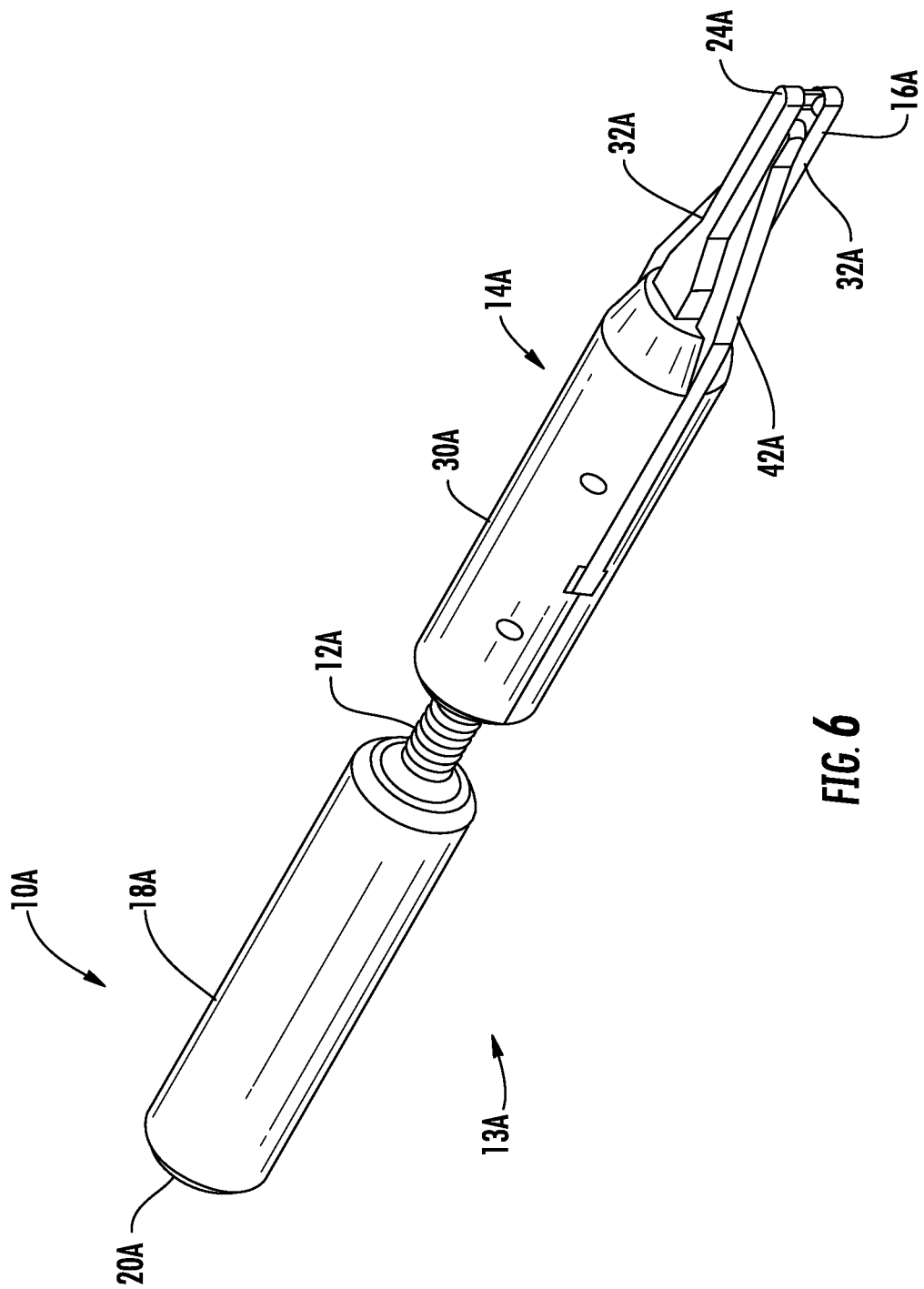
FIG. 6 is a perspective view of the pedicle screw removal device of FIG. 4.
Figure 7:
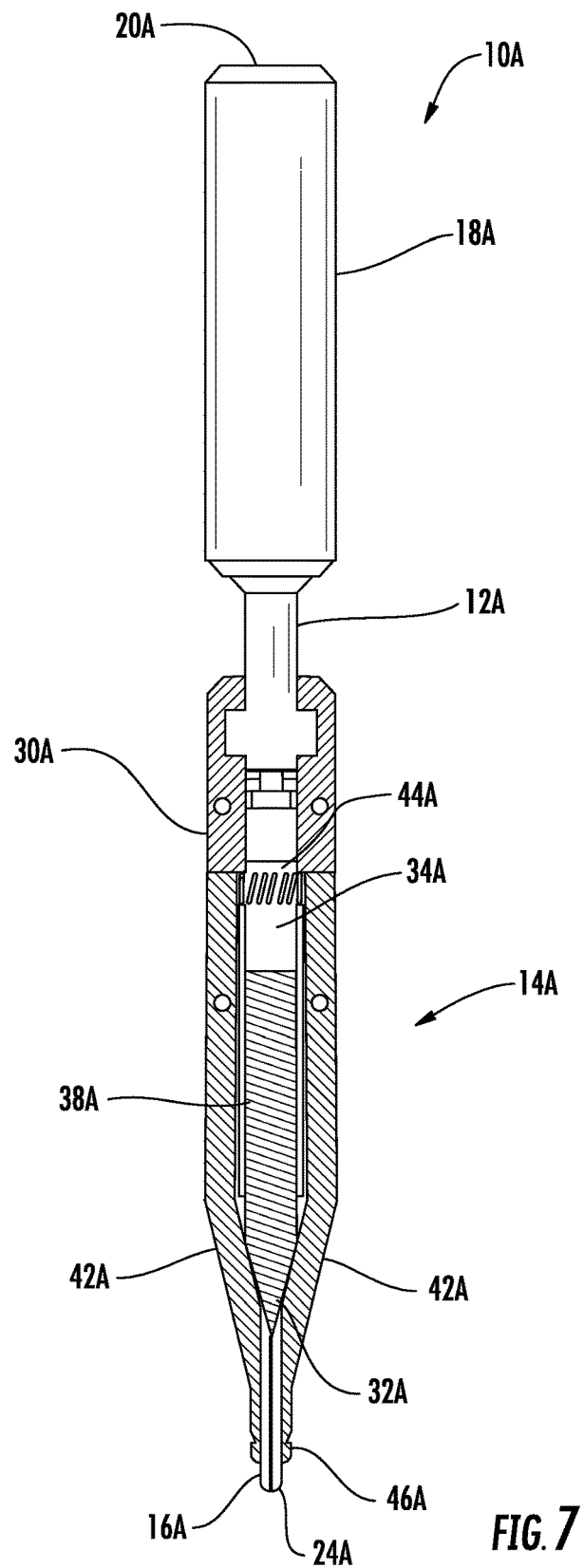
FIG. 7 is a sectional view of the pedicle screw removal device of FIG. 4.
Figure 8:
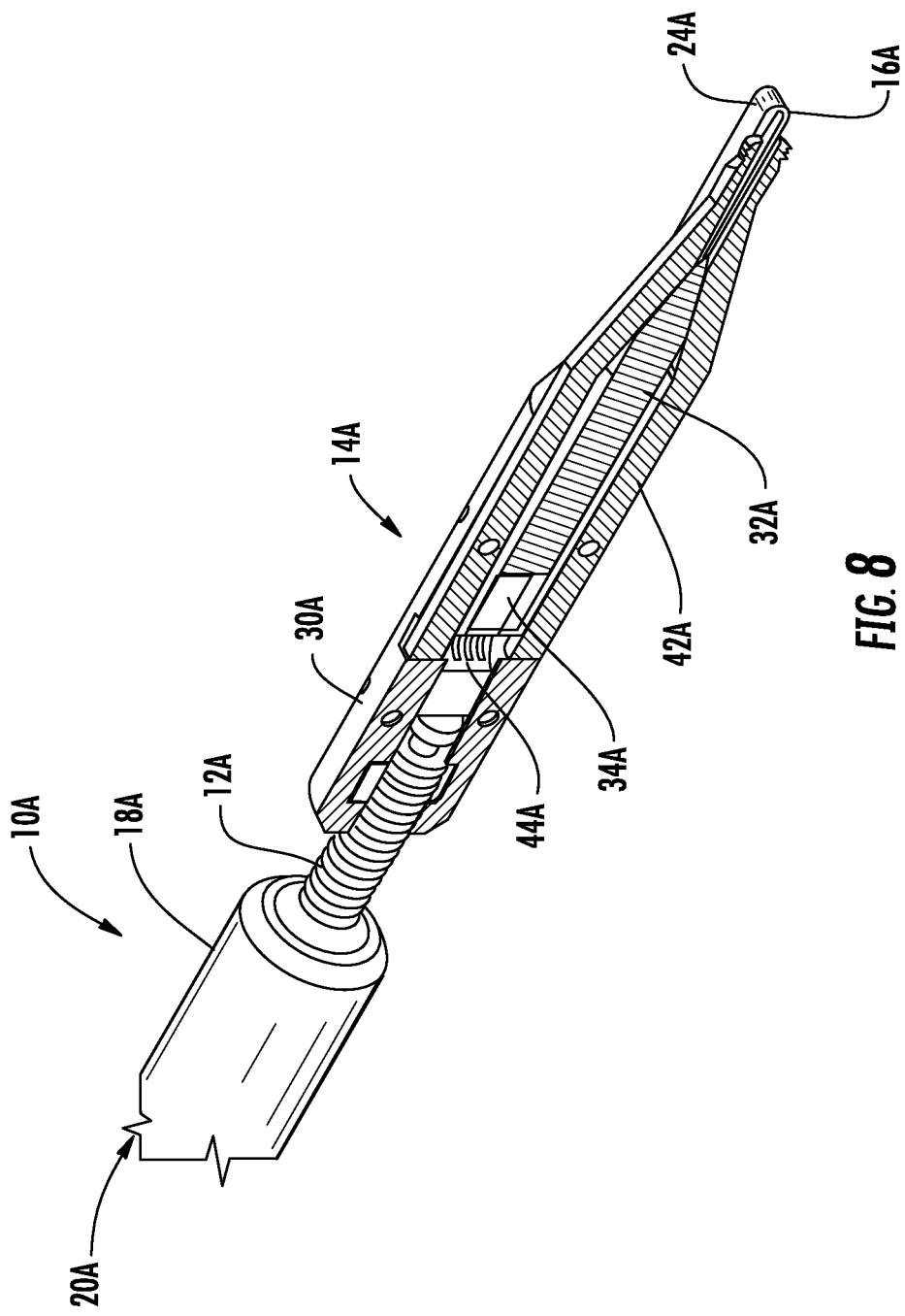
FIG. 8 is perspective sectional view of the pedicle screw removal device of FIG. 4.

According to an embodiment of the present invention, and referring to FIGS. 1-3, the pedicle screw removal device 10 includes a rod 12, a clamping member 14 located at a first end 16 of the rod 12 and a handle 18 on a second end 20 of the rod 12 opposite the clamping member 14. The pedicle screw removal device 10 clamps to a pedicle screw socket 26 to unscrew and remove a pedicle screw 22.

The rod 12 is elongated, and a substantially circular or square cross-section is preferred, though other cross-sections will be possible. A screw engagement surface 24 is integrally formed at the first end 16 of the rod 12, stabilizing the polyaxial pedicle screw 22 once the rod 12 is inserted into a pedicle screw socket 26 and pushed against the head of the pedicle screw 22. The rod 12 further includes an integrated gear track 28 at the first end portion of the rod 12, allowing the clamping member 14 to be engaged with the rod 12. Metal is the preferred material for rod 12, but any suitably durable material can also be used. The screw engagement surface 24 has a preferred diameter of 3-10 mm.

In one embodiment of the present invention, the clamping member 14 includes a sleeve 30 and a lever 32. The sleeve 30 is open-ended and defines a rod guide area 34, allowing the rod 12 to be inserted therethrough. The dimensions are such that the rod 12 is closely accommodated in the rod guide area 34. The sleeve 30 surrounds and moves along the rod 12. It will advantageous for the design and configuration of sleeve 30 to be such that it is split into two sections, each clamping to the inner or outer surface of the pedicle screw socket 26.

The lever 32 is configured at the top end of the sleeve 30, providing locking and clamping mechanisms for the clamping member 14. When the lever 32 is pulled away from the sleeve 30, the lever 32 disengages from the integrated gear track 28 of the rod 12 and unlock a sleeve lock (not shown), making the clamping member unsplittable. Thus, the clamping member 14 can move along (e.g., slide over, screw along, etc.) the rod 12. When the lever 32 is pushed toward the sleeve 30, the lever 32 can engage the gear track 28, stabilize the sleeve 30, and engage the sleeve lock (not shown) such that each half of the sleeve 30 is tightly clamped to the outer surface of the pedicle screw socket 26, as shown in FIG. 2.

Referring to FIG. 3, in an alternate embodiment of the present invention, the clamping member 14 can be designed and configured to clamp the pedicle screw 22 from an inner surface of the pedicle screw socket 26. A clamping surface 36 is formed and extends outwardly from the bottom end of a sleeve wall 38. When the lever 32 is pulled away the clamping member 14, the clamping member 14 can be lowered into the pedicle screw socket 26. The lever 32 can then pushed toward the sleeve 30 such that it can split into two half sections, each pushing against the inner surface of the pedicle screw socket 26. Other adjustment mechanisms, collars or the like could be used for releasable clamping of the sleeve 30 to the inner or outer surface of the socket 26.

In the embodiment depicted in FIGS. 1-3, the handle 18 comprises an ergonomically-shaped knob, though other shapes are possible, for example, a T-shaped knob. The size of the knob will be such that it will fit comfortably in a user's hand.

Referring to FIGS. 4-15, according to anther embodiment of the invention, the rod 12A has screw threads designed to connect to the clamp member 14A on the first end and the handle 18A on the second end by the respective matching conforming thread.

Figure 9:
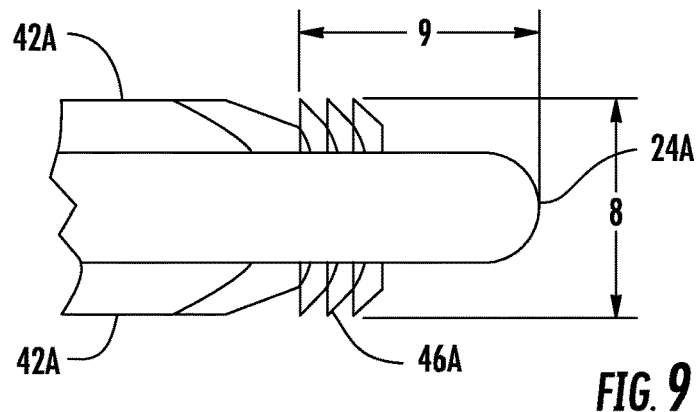
FIG. 9 is a side sectional view of the first end of the pedicle screw removal device of FIG. 4 in extended position.
Figure 10:
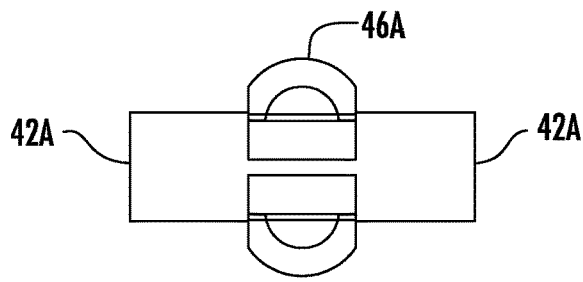
FIG. 10 is a bottom view of the pedicle screw removal device of FIG. 4 in extended position.
Figure 11:
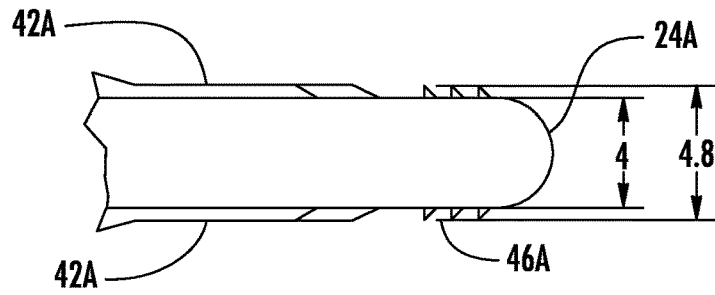
FIG. 11 is a side view of the pedicle screw removal device of FIG. 4 in retracted position.
Figure 12:
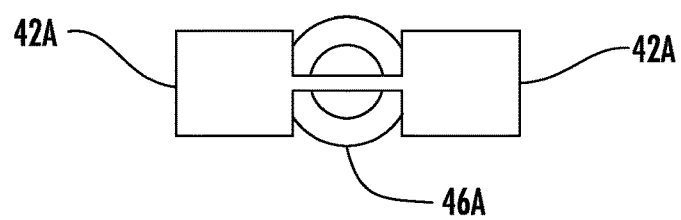
FIG. 12 is a bottom view of the pedicle screw removal device of FIG. 4 in retracted position.

The clamp member 14A comprises the sleeve 30A, the lever 32A and a pair of clamping arms 42A. The sleeve 30A is dimensioned so as to conform to the rod guide area 34A and thus closely accommodate the rod 12A and the lever 32A. The sleeve 30A and the lever 32A can move (e.g., screw) along the rod 12A in the rod guide area 34. The pair of clamping arms 42A is attached to the lever 32A via a spring biased mechanism 44A. In the depicted embodiment, the lever 32A is wedge-shaped, wider at the upper side and tapering toward the bottom apex with an elongated protrusion 24A formed extending from the apex. As such, the pair of clamping arms 42A is forced to split outwardly along a plane to an extended position, generally transverse to the longitudinal axis of the rod 12A, when the lever 32A moves downwards, as shown in FIGS. 9 and 10. Likewise, the pair of clamping arms 42A is withdrawn to a retracted position at least partially within the elongated protrusion 24A when the lever 32A moves upwards along the rod 12A, as shown in FIGS. 11 and 12.

Figure 13:
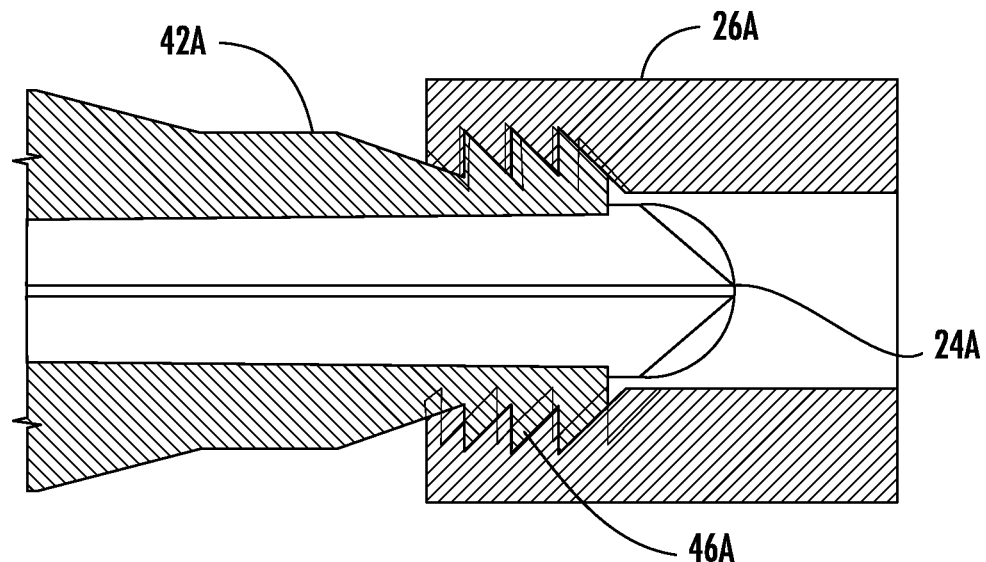
FIG. 13 is a side view of the clamping member of the pedicle screw removal device of FIG. 4 engaged with an inner surface of a pedicle screw socket.

The pair of clamping arms 42A, when in an extended position can clamp to the inner surface of the pedicle screw socket 26A, as shown in FIG. 13. The bottom end of the pair of clamping arms 42A has grooves 46A that engages grooves of the thread of an inner surface of the pedicle screw socket 26A. As such, when the pedicle screw 22 is unscrewed (see FIG. 3 for typical pedicle screw 22 and socket 26 arrangement), the grooves 46A can push against grooves of the thread of an inner surface of the pedicle screw socket 26A. In a preferred embodiment, the grooves 46A are silver soldered with carbide for enhanced durability and longevity.

Figure 14:
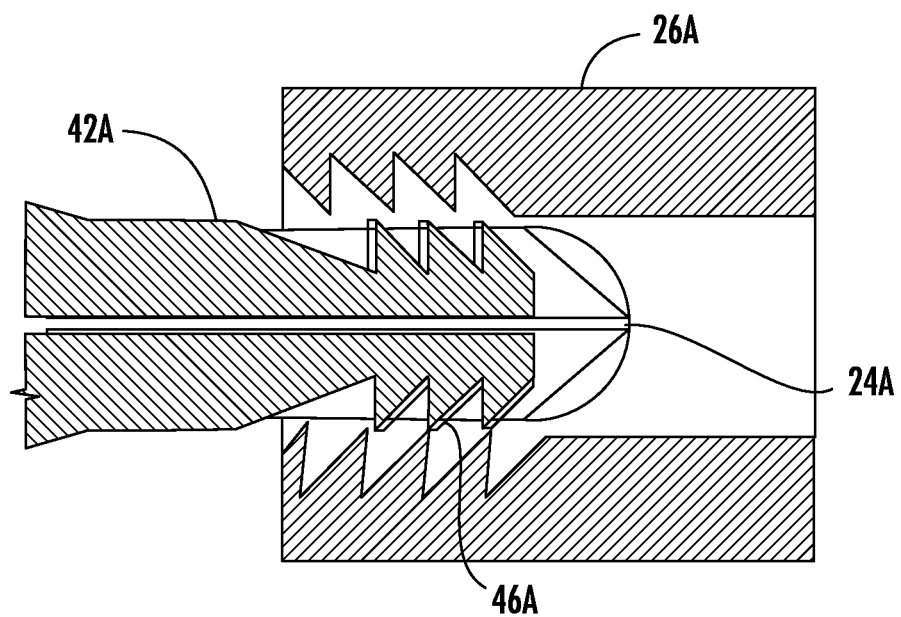
FIG. 14 is a sectional view of the clamping member of the pedicle screw removal device of FIG. 4 in a retracted position.
Figure 15:
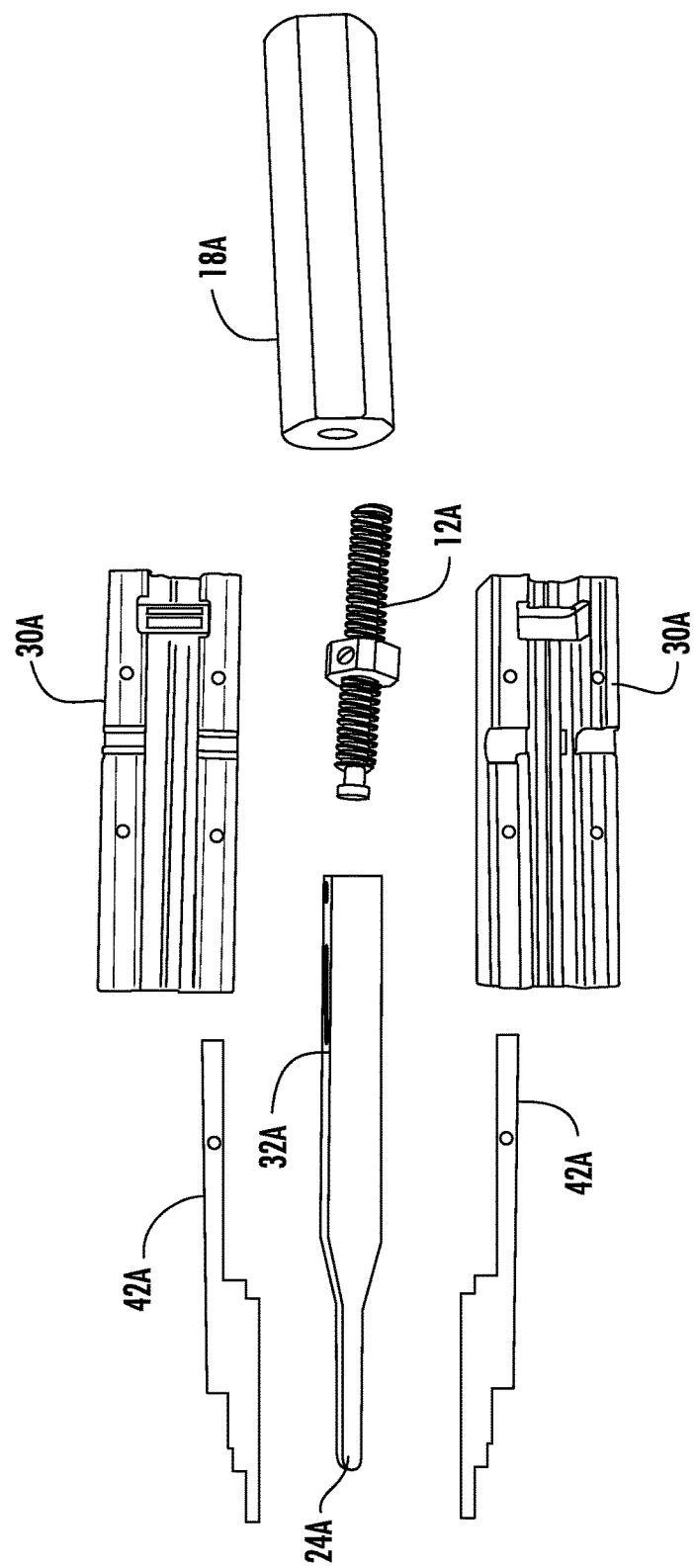
FIG. 15 illustrates components of the unassembled pedicle screw removal device of FIG. 4.

When the lever 32A moves upward, the pair of clamping arms 42A gradually moves inward from an extended position to a retracted position. The pair of arms 42A will now be closed, enabling easy withdrawn from the screw socket 26A, as shown in FIG. 14. The pair of clamping arms 42A can now transit from the extended position to the retracted position. That is, when the handle 18A is rotated clockwise, the screw head 40 is moved upward, pushing the lever 32A upwards, the distance between the pair of clamping arms 42A is reduced, enabling the pedicle removal device 10A to be withdrawn from the screw socket 26A.

Figure 16:
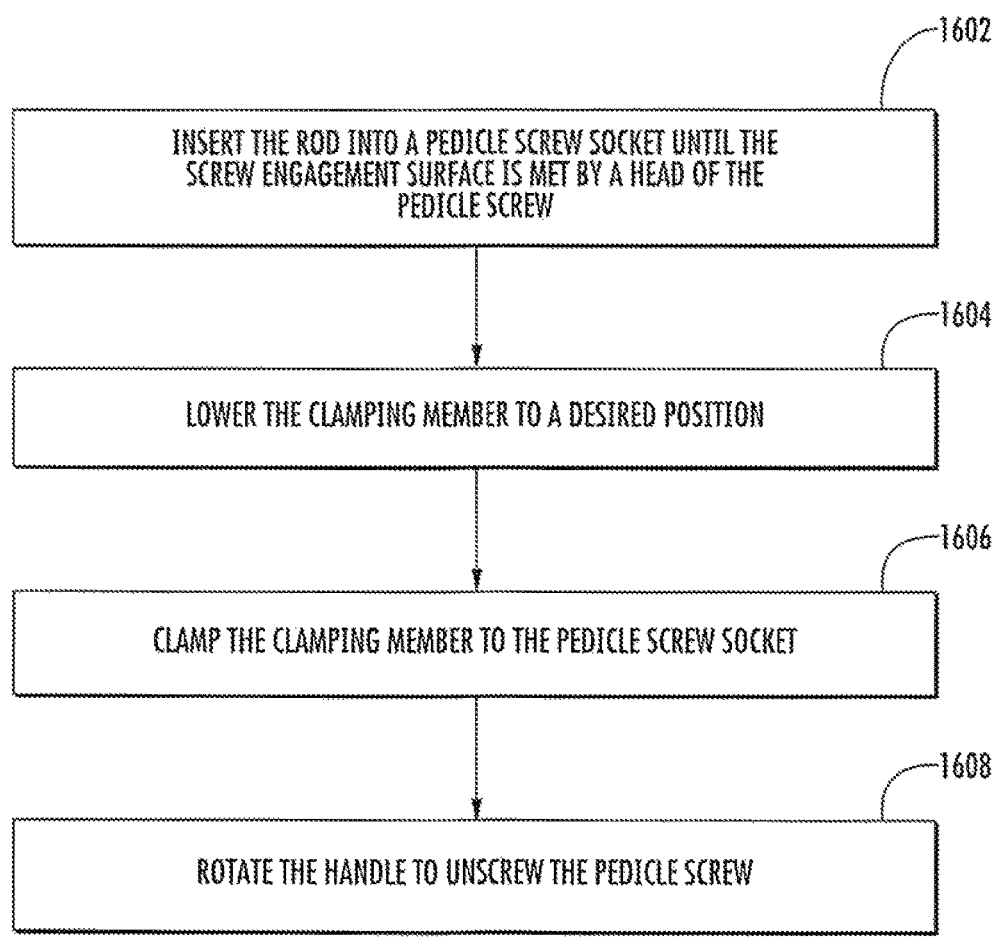
FIG. 16 is a flowchart of an exemplary method of removing a pedicle screw using a pedicle screw removal device.

Referring to FIG. 16, a method for removing a pedicle screw 22 using the pedicle screw removal device 10 is described. Before positioning the pedicle screw removal device 10 on the pedicle screw 22, a pedicle screw cap is removed from a socket 26. The rod of the previously implemented fixation system will also need to be removed from the socket 26. At step 1602, the rod 12 is inserted into the pedicle screw socket 26 until the screw engagement surface 24 of the rod 12 is met by the head 40 of the screw 22. At step 1604, the clamping member 14 is lowered to a desired position with the lever 32 moved upward along the rod 12. At step 1606, once the clamping member 14 reaches to the desired position, the lever 32 is moved downward along the rod 12, allowing the pair of clamping arms 42 to clamp to the inner surface of the pedicle screw socket 26. The bottom point of the lever 32 is pressed against the head 40 of the pedicle screw 22, firmly engaging it. At step 1608, the pedicle screw removal device 10 is then rotated with the handle 18, unscrewing and removing the pedicle screw 22. The pedicle screw removal device 10 can be used to remove any type or size of polyaxial pedicle screw.

From the foregoing, it will be appreciated that a pedicle screw removal device according to the present invention enables the easy removal of a polyaxial pedicle screw by effective locking of the pedicle screw against the socket and removing both as a single unit. Moreover, the device is readily adaptable to a wide range of pedicle screw sizes from a variety of manufacturers. The present invention thus eliminates the need for a surgeon to have a wide range of manufacturer-specific tools on hand to remove a pedicle screw. The invention will be particularly useful in cases where the manufacturer(s) of such screws are unknown until after surgery has commenced, if they can be identified then.

In general, the foregoing description is provided for exemplary and illustrative purposes; the present invention is not necessarily limited thereto. Rather, those skilled in the art will appreciate that additional modifications, as well as adaptations for particular circumstances, will fall within the scope of the invention as herein shown and described and of the claims appended hereto.

What is claimed is:

1. A pedicle screw removal device comprising:
   a rod extending along a longitudinal axis between a first end and a second end opposite the first end;
   a clamping member located at the first end of the rod; and
   a handle located at the second end of the rod;
   wherein the clamping member is configured to clamp to a pedicle screw socket;
   wherein the clamping member comprises a sleeve, a pair of clamping arms, and a lever;
   wherein the pair of clamping arms are mounted to the sleeve and movable between an extended position, in which the clamping arms are split outwardly transverse to the longitudinal axis of the rod, and a retracted position, in which the clamping arms are withdrawn inwardly from the extended position;
   wherein the lever is movable within the sleeve along the longitudinal axis of the rod into a position between the clamping arms, with movement of the lever toward the first end forcing the clamping arms into the extended position and movement of the lever toward the second end allowing the clamping arms to withdraw into the retracted position; and
   wherein an elongated protrusion of the lever extends beyond the pair of clamping arms along the longitudinal axis, such that distal ends of the pair of clamping arms are, transverse to the longitudinal axis, at least partially withdrawn behind the elongated protrusion in the retracted position.

2. The pedicle screw removal device of claim 1, wherein the clamping member moves along the first end portion of the rod.

3. The pedicle screw removal device of claim 1, wherein a screw engagement surface is integrally formed at the first end of the rod.

4. The pedicle screw removal device of claim 3, wherein the screw engagement surface has a diameter between 3 mm-10 mm.

5. The pedicel screw removal device of claim 1, wherein the pair of clamping arms is connected by a spring biased mechanism.

6. The pedicle screw removal device of claim 1, wherein the rod is dimensioned to be accommodated in a rod guide area defined by the sleeve.

7. The pedicle screw removal device of claim 1, wherein the clamping member is configured to clamp to an inner surface of a pedicle screw socket.

8. A method of removing a pedicle screw using the pedicle screw removal device of claim 1, the method comprising:
   inserting the rod into a pedicle screw socket until the screw engagement surface is met by a head of the pedicle screw;
   lowering the clamping member to a desired position;
   engaging the clamping member to the pedicle screw socket; and
   rotating the handle to unscrew the pedicle screw while pressing the head of the pedicle screw.

9. The method of removing a pedicle screw of claim 8, wherein the clamping member is lowered to a desired position while the clamping member is in a retracted position.

10. The method of removing a pedicle screw of claim 8, wherein the clamping member is clamped to the pedicle screw socket while the clamping member is in an extended position.

11. The method of removing a pedicle screw of claim 8, wherein the clamping member comprises engaging the clamping member to an inner surface of a pedicle screw socket.

12. The method of removing a pedicle screw of claim 11, wherein engaging the clamping member to the inner surface of a pedicle screw socket comprises moving the lever of the clamping member toward the pedicle screw socket.

13. The method of removing a pedicle screw of claim 8, further comprising removing one or more of a pedicle screw cap and fixation system of the pedicle screw socket prior to inserting the rod into the pedicle screw socket.

\* \* \* \* \*